United States Patent
Kang et al.

(10) Patent No.: US 9,719,959 B2
(45) Date of Patent: Aug. 1, 2017

(54) HYDROGEN ION SENSOR

(71) Applicant: Kyungpook National University Industry-Academic Cooperation Foundation, Daegu (KR)

(72) Inventors: Shin-Won Kang, Daegu (KR);
Hyun-Min Jeong, Daegu (KR);
Hyeon-Ji Yun, Daegu (KR);
Hyurk-Choon Kwon, Gyeongsangbuk-do (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 17 days.

(21) Appl. No.: 14/546,476

(22) Filed: Nov. 18, 2014

(65) Prior Publication Data

US 2015/0137190 A1  May 21, 2015

(30) Foreign Application Priority Data

Nov. 18, 2013  (KR) .......................... 10-2013-0140109

(51) Int. Cl.
*H01L 29/788* (2006.01)
*G01N 27/414* (2006.01)

(52) U.S. Cl.
CPC .................. *G01N 27/414* (2013.01)

(58) Field of Classification Search
CPC ................................................ G01N 27/414
See application file for complete search history.

(56) References Cited

U.S. PATENT DOCUMENTS 8,283,736 B2 * 10/2012 Kang ................. G01N 27/4148
257/414

FOREIGN PATENT DOCUMENTS

| KR | 10-1050761 B1 | 7/2011 |
| KR | 20110122323 A | 11/2011 |
| KR | 20120000369 A | 1/2012 |
| KR | 10-2012-0038041 A | 4/2012 |

OTHER PUBLICATIONS

Kwon et al., "The Characteristics of H + Ion-Sensitive Transistor Driving With MOS Hybrid Mode Operation", IEEE Electron Device Letters, vol. 29, No. 10, Oct. 2008, pp. 1138-1141.

(Continued)

*Primary Examiner* — Long Pham
(74) *Attorney, Agent, or Firm* — Carter, DeLuca, Farrell & Schmidt, LLP

(57) ABSTRACT

Provided is a hydrogen ion sensor including: a substrate having a well and a first contact, the well having a second, a third, a fourth and a fifth contacts, the second contact having the same conductive type as the well, and the third, the fourth, and the fifth contacts having an opposite conductive type to the well; a first gate insulation layer on a region between the fourth contact and the fifth contact; a second gate insulation layer on a region between the third contact and the fourth contact; and a hydrogen ion sensing unit formed on the first gate insulation layer, wherein the hydrogen ion sensing unit transfers a voltage level adjusted according to a hydrogen ion concentration of a solution to be measured, to the first gate insulation layer.

11 Claims, 11 Drawing Sheets

(56) References Cited

OTHER PUBLICATIONS

Wong, "Matching Properties and Applications of Compatible Lateral Bipolar Transistors (CLBTs)", A Thesis Submitted in Partial Fulfillment of the Requirements for the Degree of Master of Philosophy in the Computer Science and Engineering Department, The Chinese University of Hong Kong, Jul. 2001, pp. 1-111.

Yuan et al., "Sensitivity Alterable Biosensor Based on Gated Lateral BJT for CRP Detection", Journal of Semiconductor Technology and Science, vol. 13, No. 1, Feb. 2013, pp. 434-437.

Yuan et al., "Highly sensitive ion sensor based on the MOSFET-BJT hybrid mode of a gated lateral BJT", Sensors and Actuators B 181 (2013), pp. 44-49.

Yuan et al., "Room temperature VOC gas detection using a gated lateral BJT with an assembled solvatochromic dye", Sensors and Actuators B 187 (2013), pp. 288-294.

Lin et al., "Lateral Complementary Transistor Structure for the Simultaneous Fabrication of Functional Blocks", Proceedings of the IEEE, Dec. 1964, pp. 1491-1496.

Parke et al., "Bipolar-FET Hybrid-Mode Operation of Quarter-Micrometer SOI MOSFET's", IEEE Electron Device Letters, vol. 14, No. 5, May 1993, pp. 234-236.

Shine et al., "Solid phase radioimmunoassay for human C-reactive protein", Clinicu Chimicu Acta, 117 (1981), pp. 13-23.

Yuan et al., "MOSFET-BJT hybrid mode of the gated lateral bipolar junction transistor for C-reactive protein detection", Biosensors and Bioelectronics 28 (2011) 434-437.

\* cited by examiner

HYDROGEN ION SENSOR

CROSS-REFERENCE TO RELATED APPLICATIONS

This U.S. non-provisional patent application claims priority under 35 U.S.C. §119 of Korean Patent Application No. 10-2013-0140109, filed on Nov. 18, 2013, the entire contents of which are hereby incorporated by reference.

BACKGROUND OF THE INVENTION

The present invention relates to a hydrogen ion sensor, and more particularly, to a CMOS semiconductor hydrogen ion sensor based on a gated lateral bipolar junction transistor (GLBJT).

A hydrogen ion sensor is used for a purpose for measuring a concentration (for example, pH) of hydrogen ions for process control, a vivo assay and clinical analysis, an environmental monitoring or the like in various industry fields including chemical industry, public health, agriculture, fishery, and biology-related industry. pH is a parameter significantly considered when a characteristic of a solution to be measured is determined, and is an essential factor in understanding a chemical reaction or a chemical characteristic of a solution. A pH sensor is used for quantitatively measuring power of hydrogen (pH) that is a logarithm value of a hydrogen ion concentration of a solution to be measured. Recently, new concept semiconductor elements capable of measuring a hydrogen ion concentration have been reported. In an example, disclosed is a hydrogen ion sensing element using an arrayed gated lateral BJT in Korean Pat. No. 1050761.

SUMMARY OF THE INVENTION

The present invention provides a high sensitivity hydrogen ion sensor capable of remarkably improving sensitivity with respect to a hydrogen ion concentration.

The present invention also provides a high sensitivity hydrogen ion sensor capable of quantitatively sensing the concentration of a trace of hydrogen ion.

Effects of the present invention are not limited to the aforesaid, but other effects not described herein will be clearly understood by those skilled in the art from descriptions below.

Embodiments of the present invention provide hydrogen ion sensor comprising: a substrate having a well and a first contact, the well having a second, a third, a fourth and a fifth contacts, the second contact having the same conductive type as the well, and the third, the fourth, and the fifth contacts having an opposite conductive type to the well; a first gate insulation layer on a region between the fourth contact and the fifth contact; a second gate insulation layer on a region between the third contact and the fourth contact; and a hydrogen ion sensing unit on the first gate insulation layer, wherein the hydrogen ion sensing unit transfers a voltage level adjusted according to a hydrogen ion concentration of a solution to be measured, to the first gate insulation layer.

In some embodiments, the hydrogen ion sensor may further comprise a first conductive layer on the first gate insulation layer; and a second conductive layer on the second gate insulation layer.

In other embodiments, the first gate insulation layer and the first conductive layer may have a ring shape surrounding the fifth contact, and the second gate insulation layer and the second conductive layer may have a ring shape surrounding the fourth contact.

In still other embodiments, the hydrogen ion sensing unit may comprise: a reference electrode contacting the solution to be measured, and to which a predetermined reference voltage is applied; a measurement electrode measuring the voltage level adjusted according to the hydrogen ion concentration; and a floating gate on the first gate insulation layer and transferring the voltage level to the first conductive layer.

In even other embodiments, the measurement electrode may comprise; a first metal layer; and a passivation layer on the first metal layer, wherein the passivation layer comprises a silicon nitride layer.

In yet other embodiments, the floating gate may comprise a plurality of second metal layers connected to each other through vias.

In further embodiments, the well, the fourth contact, the fifth contact and the first gate insulation layer may constitute a first field effect transistor, the well, the second contact, the fourth contact and the fifth contact may constitute a first bipolar junction transistor, the substrate, the well, the first contact, the second contact and the fifth contact may constitute a second bipolar junction transistor, and the well, the third contact, the fourth contact, and the second gate insulation layer may constitute a second field effect transistor that is connected in a cascode structure to the first field effect transistor and the first bipolar junction transistor.

In still further embodiments, the second filed effect transistor may be a field effect transistor of a N-channel type or a P-channel type.

In even further embodiments, the first contact may operate as a collector terminal of the second bipolar junction transistor, the second contact may operate as a base terminal of the first bipolar junction transistor and the second bipolar junction transistor, the third contact may operate as a drain terminal of the second field effect transistor, the fourth contact may operate as a drain terminal of the first field effect transistor, a source terminal of the second field effect transistor and a collector terminal of the first bipolar junction transistor, and the fifth contact may operate as a source terminal of the first field effect transistor and an emitter terminal of the first bipolar junction transistor and the second bipolar junction transistor.

In yet further embodiments, an operating point of the first bipolar junction transistor and the second bipolar junction transistor may be adjusted by a bias current applied on the second contact.

In much further embodiments, the hydrogen ion concentration may be detected by detecting an amount of a current flowing through the fifth contact.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
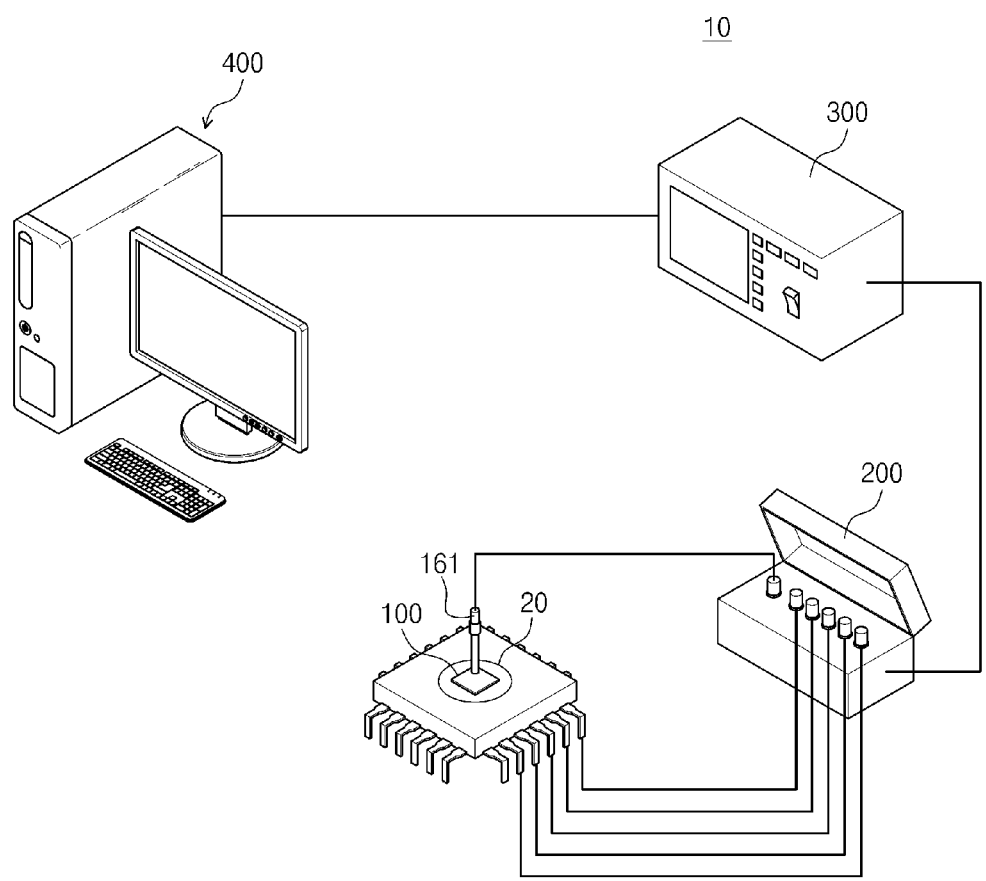
FIG. 1 is a view illustrating a hydrogen ion sensing system including a hydrogen ion sensor according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims.

Though not defined, all terms (including technical or scientific terms) used herein have the same meanings as those generally accepted by universal technologies in the related art to which the present invention pertains. The terms defined by general dictionaries may be construed as having the same meanings as those in the related art and/or the text of the present application, and will not be construed as being conceptualized or excessively formal although the terms are not clearly defined expressions herein. Moreover, detailed descriptions related to well-known functions or configurations will be ruled out in order not to unnecessarily obscure subject matters of the present invention. In the drawings, like reference numerals refer to like elements throughout.

A hydrogen ion sensor according to an embodiment of the present invention comprises a first conductive type substrate; a second conductive type well and a first conductive type first contact in the substrate; a second conductive type second contact, a third, a fourth and a fifth contacts of the first conductive type in the well; a first gate insulation layer on a region between the fourth contact and the fifth contact; a second gate insulation layer on a region between the third contact and the fourth contact; and a hydrogen sensing unit on the first gate insulation layer. In an embodiment of the present invention, the fourth contact and the fifth contact constitute a first field effect transistor, the second contact, the fourth contact and the fifth contact constitute a first bipolar junction transistor, and the first contact, the second contact and the fifth contact constitute a second bipolar junction transistor.

The hydrogen ion sensor according to an embodiment of the present invention is configured such that the third contact is disposed between the second contact and the fourth contact, and the third contact and the fourth contact constitute a second field effect transistor. Therefore, in the hydrogen ion sensor according to an embodiment of the present invention, since the second field effect transistor (the third and fourth contacts) is formed in a cascode series structure together with the first field effect transistor (the fourth and fifth contacts), the first bipolar junction transistor (the second, fourth and fifth contacts) and the second bipolar junction transistor (the first, second and fifth contacts), a transconductance characteristic of a CMOS element is improved, and thus a sensitivity characteristic with respect to a hydrogen ion is remarkably improved.

FIG. 1 is a view illustrating a hydrogen ion sensing system including a hydrogen ion sensor according to an embodiment of the present invention. Referring to FIG. 1, a hydrogen ion sensing system 10 may be provided as a semiconductor type hydrogen ion sensing system, and measure a hydrogen ion concentration (for example, pH) of a solution 20 to be measured. For example, the solution 20 to be measured may be an electrolyte solution. The hydrogen ion sensing system 10 may include a hydrogen ion sensor 100, a test fixture 200, a semiconductor parameter analyzer 300, and an analysis computer 400. The hydrogen ion sensor 100 may be prepared by being manufactured in a chip type through a complementary metal-oxide semiconductor (CMOS) process and bonded on a printed circuit board (PCB), and may be sealed with an epoxy except for a hydrogen sensing unit (see reference numeral 160 of FIG. 2).

The test fixture 200 may apply a reference voltage to a reference electrode 161 in order to measure a hydrogen ion concentration of a solution 20 to be measured under an electric and optical shield environment, and receive a measurement value of the hydrogen ion sensor 100 outputted according to the hydrogen ion concentration of the solution 20 to be measured and supply the measurement value to the semiconductor parameter analyzer 300. The semiconductor parameter analyzer 300 may measure the hydrogen ion concentration of the solution 20 to be measured by using the measurement value of the hydrogen ion sensor 100, and supply an analysis result to the analysis computer 400. The analysis computer 400 may display the hydrogen ion concentration of the solution 20 to be measured, or information on various parameters of the CMOS chip on a screen thereof.

Figure 2:
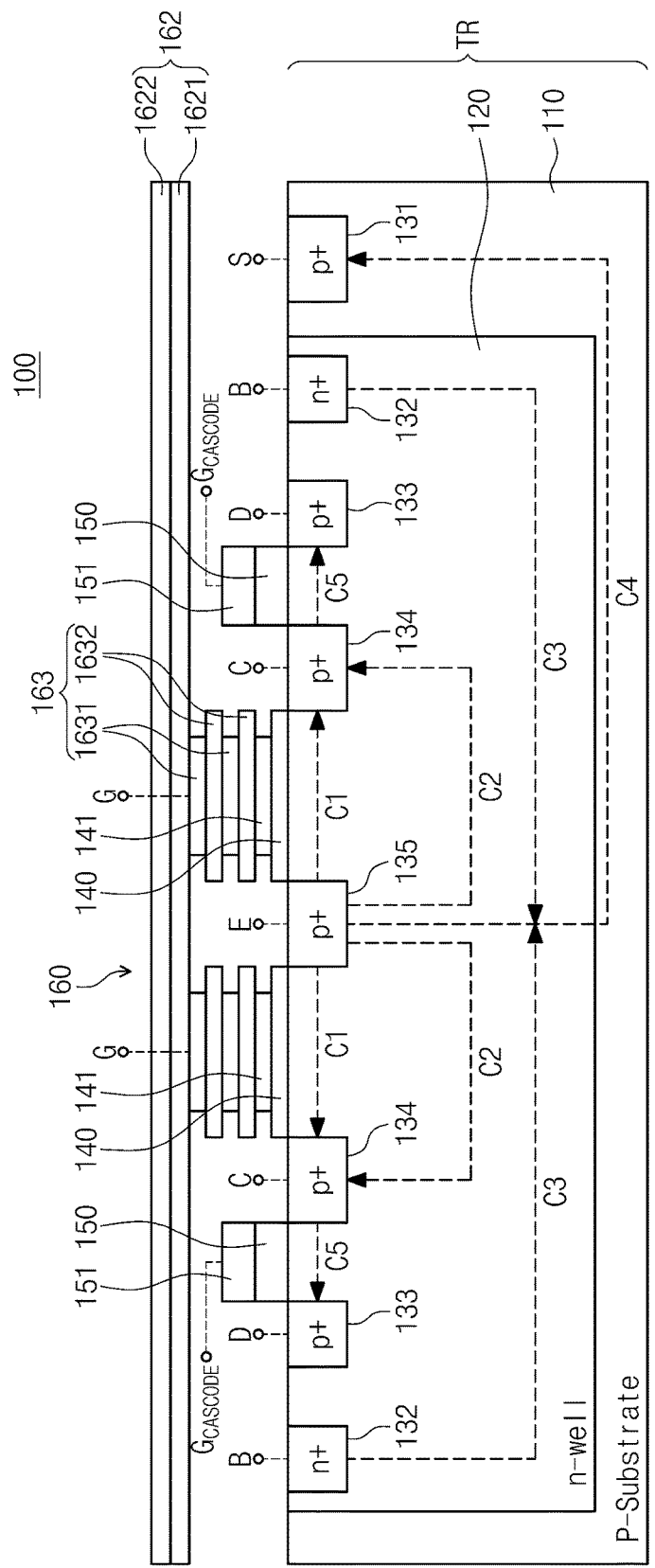
FIG. 2 is a perspective view illustrating a hydrogen ion sensor according to an embodiment of the present invention.

FIG. 2 is a cross-sectional view illustrating a hydrogen ion sensor according to an embodiment of the present invention. A hydrogen ion sensor 100 according to an embodiment of the present invention includes a substrate 110, a well 120, first to fifth contacts 131 to 135, a first gate insulation layer 140, a first conductive layer 141, a second gate insulation layer 150, a second conductive layer 151 and a hydrogen ion sensing unit 160. The hydrogen ion sensor 100 according to an embodiment of the present invention has both of a characteristic of a bipolar junction transistor (BJT) and a characteristic of a metal oxide silicon field effect transistor (MOSFET), and may be provided in a gated lateral bipolar junction transistor (GLBJT) structure manufactured using CMOS process. This will be later described in more detail with reference to FIGS. 3 and 4.

The substrate 110 may be a silicon substrate doped with a first conductive type (for example, a P conductive type) impurity. The well 120 may be provided in the substrate 110. The well 120 may be provided in silicon doped with a second conductive type (for example, a N conductive type) impurity different from that of the substrate 110. For example, A Group V element such as phosphorus (P) may be injected into the substrate 110 to form the well 120.

The first contact 131 may be provided in an upper portion of a region except for the well 120 among regions on the substrate 110. The first contact 131 may be provided in the silicon substrate doped with a first conductive type (for example, a P conductive type) impurity in the same manner as the substrate 110. For example, a Group III element such as boron (B) may be doped on the substrate 110 to form the first contact 131.

In an embodiment, the first contact 131 may have a doping concentration higher than that of the substrate 110. In an embodiment, the first contact 131 may be used as an electrode for forming a ground on the substrate 110.

The second to fifth contacts 132 to 135 may be provided on an upper portion of the well 120. For example, the third contact 133, the fourth contact 134 and the fifth contact 135 may be sequentially provided in a direction directed from the second contact 132 to the fifth contact 135. For example, the fourth contact 134 may be disposed on a position spaced apart from the fifth contact 135 while surrounding the fifth contact 135 in a ring shape, the third contact 133 may be disposed on a position spaced apart from the fourth contact 134 while surrounding the fourth contact 134 in a ring shape, and the second contact 132 may be disposed on a position spaced apart from the third contact 133 while surrounding the third contact 133 in a ring shape.

The second contact 132 may be provided in the silicon substrate doped with a second conductive type (for example, a N conductive type) impurity in the same manner as the well 120. For example, a Group V element such as phosphorus (P) may be doped on an upper portion the well 110 to form the second contact 132.

For example, the second contact 132 may have a doping concentration higher than that of the well 120. For example, the second contact 132 may be used as an electrode supplying electric power (for example, a base current) to the well 120. The third to fifth contacts 133 to 135 may be provided in the silicon doped with a first conductive type (for example, a P conductive type) impurity in the same manner as the substrate 110. For example, a Group III element such as boron (B) may be doped on an upper portion of the well 120 to form third to fifth contacts 133 and 135.

The first gate insulation layer 140 may be disposed on a region between the fourth contact 134 and the fifth contact 135. The first conductive layer 141 may be disposed on the first gate insulation layer 140. In an embodiment, the first gate insulation layer 140 and the first conductive layer 141 may be formed so as to have a ring shape surrounding the fifth contact 135.

The second gate insulation layer 150 may be disposed on a region between the third contact 133 and the fourth contact 134. The second conductive layer 151 may be disposed on the second gate insulation layer 150. The second gate insulation layer 150 and the second conductive layer 151 may be formed so as to have a ring shape surrounding the fourth contact 134. For example, the first and second gate insulation layers 140 and 150 may include silicon oxide ($SiO_2$). For example, the first and second conductive layers 141 and 151 may include poly silicon.

The hydrogen ion sensing unit 160 may be disposed on the first conductive layer 141. The hydrogen ion sensing unit 160 may transfer a voltage level adjusted according to a hydrogen ion concentration of the solution (see reference numeral 20 of FIG. 1) to be measured to the first conductive layer 141 and the first gate insulation layer 140. The hydrogen ion sensing unit 160 may include a reference electrode 161, a measurement electrode 162 and a floating gate 163.

The reference electrode 161 may be provided to contact the solution 20 to be measured and to be spaced apart from the measurement electrode 162. A predetermined reference voltage may be applied on the reference electrode 161. The reference electrode 161 may be provided in the form of a conductive material, such as silver (Ag)/silver chloride (AgCl), gold (Au), palladium (Pd), platinum (Pt) or the like, for example, a precious metal. A surface potential of the measurement electrode 162 may be adjusted according to a hydrogen ion concentration. That is, the surface potential of the measurement electrode 162 is changed according to a hydrogen ion concentration of the solution 20 to be measured by an electrochemical reaction, and thus the hydrogen ion concentration may be measured from a change of a current amount that flows in the fifth contact 135. For example, the measurement electrode 162 may include a metal, such as gold (Au), palladium (Pd) or platinum (Pt). In an example, the measurement electrode 162 may be formed so as to have an area greater than that of the first conductive layer 141 operating as a gate terminal G, and thus detection performance of the hydrogen ion sensor 100 may be improved.

In an embodiment of the present invention, the measurement electrode 162 may be provided with a metal layer 1621 and a passivation layer 1622. The passivation layer 1622 may be disposed on an upper portion of the metal layer 1621, and may be stacked through a method such as a plasma enhanced chemical vapor deposition in a commonly used CMOS process. The passivation layer 1622 may include a silicon nitride layer (for example, $Si_3N_4$) or $Al_2O_3$. The passivation layer 1622 may induce a site-binding phenomenon, and a potential of the floating gate 163 may be changed according to a change of the surface potential.

The floating gate 163 is disposed on the first conductive layer 141 so as to operate as an ion detection gate, and transfers a voltage level applied on the measurement electrode 162, to the first conductive layer 141 and the first gate insulation layer 140. The floating gate 163 may be comprised of a plurality of metal layers 1632 connected to each other through vias 1631. A floating gate 163 structure is suitably applied to a process having a gate width that is a nano unit compared to an open gate structure.

Figure 3:
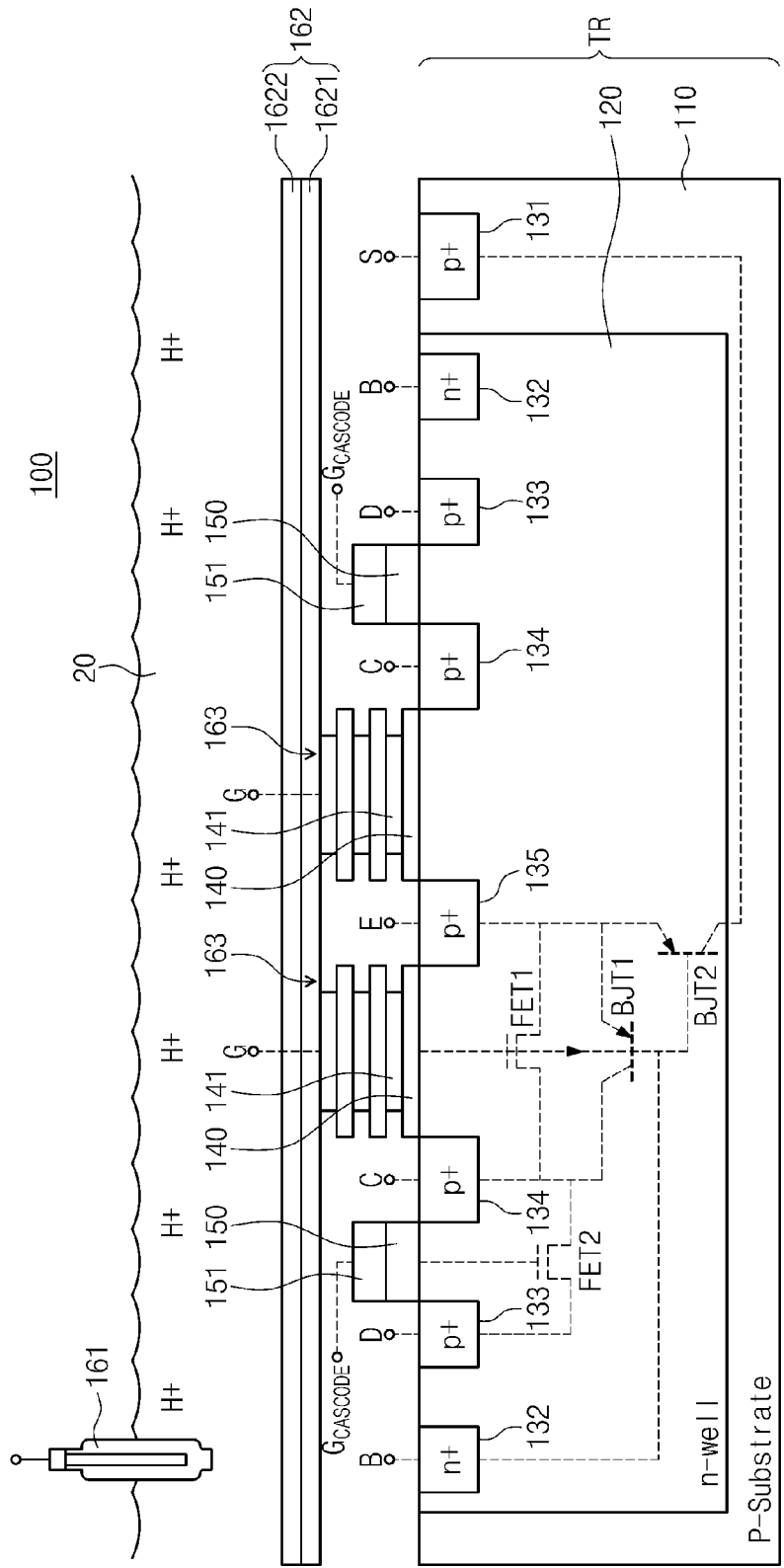
FIG. 3 is a cross-sectional view illustrating a hydrogen ion sensor according to an embodiment of the present invention.

FIG. 3 is a cross-sectional view illustrating a hydrogen ion sensor according to an embodiment of the present invention. In order to help understanding of the present invention, an equivalent circuit of a first field effect transistor FET1 constituted by the well 120, the fourth contact 134, the first gate insulation layer 140 and the first conductive layer 141, a first bipolar junction transistor BJT1 constituted by the well 120, the second contact 132, the fourth contact 134 and the fifth contact 135, a second bipolar junction transistor BJT2 constituted by the substrate 110, the well 120, the first contact 131, the second contact 132 and the fifth contact 135, and a second field effect transistor FET2 constituted by the well 120, the third contact 133, the fourth contact 134, the second gate insulation layer 150 and the second conductive layer 151 is illustrated in a dashed line in FIG. 3.

Figure 4:
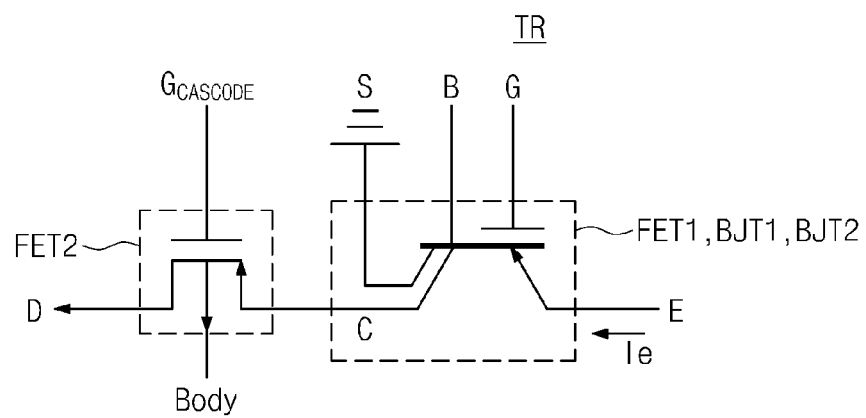
FIG. 4 is a view illustrating an equivalent circuit diagram of a hydrogen ion sensor according to an embodiment of the present invention.

FIG. 4 is a view illustrating an equivalent circuit diagram of a hydrogen ion sensor according to an embodiment of the present invention. Referring to FIGS. 3 and 4, the second field effect transistor FET2 constituted by the well 120, the third contact 133, the fourth contact 134, the second gate insulation layer 150 and the second conductive layer 151 is connected to the first field effect transistor FET1 and the first bipolar junction transistor BJT1 in series in a cascode structure. Thus, since a transconductance characteristic of a CMOS semiconductor is improved and sensitivity with respect to a hydrogen ion concentration is improved, the minimum of the hydrogen ion concentration may be quantitatively sensed.

Referring to FIGS. 2 to 4, in an embodiment of the present invention, the well 120 may operate as a body of the first field effect transistor FET1, the fourth contact 134 and the fifth contact 135 may operate as a drain terminal and a source terminal of the first field effect transistor FET1 respectively, the first gate insulation layer 140 may operate as a gate insulation layer of the first field effect transistor FET1, and the first conductive layer 141 may operate as a gate terminal of the first field effect transistor FET1. In an embodiment, the well 120, the fourth contact 134, the fifth contact 135, the first gate insulation layer 140 and the first conductive layer 141 may operate as a P-channel type field effect transistor. However, the first field effect transistor FET1 may be designed in a N-channel type field effect transistor.

In an embodiment of the present invention, the well 120 and the second contact 132 may operate as a base terminal B of the first bipolar junction transistor BJT1, the fourth contact 134 may operate as a collector terminal C of the first bipolar junction transistor BJT1, and the fifth contact 135 may operate as an emitter terminal E of the first bipolar junction transistor BJT1. Since the collector terminal C and the emitter terminal E of the first bipolar junction transistor BJT1 constituted by the well 120, the second contact 132, the fourth contact 134 and the fifth contact 135 are disposed in a lateral shape, the first bipolar junction transistor BJT1 may be called a lateral junction transistor.

In an embodiment of the present invention, the substrate 110, the well 120 and the second contact 132 may operate as a base terminal B of the second bipolar junction transistor BJT2, the first contact 131 may operate as a collector terminal S of the second bipolar junction transistor BJT2, and the fifth contact 135 may operate as an emitter terminal E of the second bipolar junction transistor BJT2. Since the collector terminal S and the emitter terminal E of the second bipolar junction transistor BJT2 constituted by the substrate 110, the well 120, the first contact 131, the second contact 132 and the fifth contact 135 are disposed in a vertical shape, the second bipolar junction transistor BJT2 may be called as a vertical junction transistor.

In an embodiment of the present invention, the well 120 may operate as a body of the second field effect transistor FET2, the third contact 133 and the fourth contact 134 may operate as a drain terminal D and a source terminal of the second field effect transistor FET2, respectively, the second gate insulation layer 150 may operate as a gate insulation layer of the second field effect transistor FET2, and the second conductive layer 151 may be operate as a gate terminal $G_{CASCODE}$ of the second field effect transistor FET2. In an embodiment, the well 120, the third contact 133, the fourth contact 134, the second insulation layer 150 and the second conductive layer 151 may operate as a P-channel type effect transistor. However, the second field effect transistor FET2 may be designed in a N-channel type effect transistor. Flows of a channel current C1 of the first field effect transistor FET1, a channel current C5 of the second field effect transistor FET2, an emitter current (Ie) C2 of the first bipolar junction transistor BJT1, a base current C3 flowing into a base terminal of the first bipolar junction transistor BJT1 and the second bipolar junction transistor BJT2, and a collector current C4 of the second bipolar junction transistor BJT2 are illustrated in a dashed line arrow in FIG. 2. In an embodiment of the present invention, a portion except for the hydrogen ion sensing unit 160, that is, a portion including the substrate 110, the well 120, the first to fifth contacts 131 to 135, the first and second gate insulation layers 140 and 160, and the first and second conductive layers 141 and 151 may be called a transistor unit TR.

The hydrogen sensing unit 100 may operate in an FET mode, a BJT mode or a hybrid mode. For example, the first and second field effect transistors FET1 and FET2 may not operate in the BJT mode. For example, when a positive voltage is applied on the reference electrode 161, since the positive voltage is transferred to the gate terminal of the first field effect transistor FET1 from the reference electrode 161 through the solution 20 to be measured, a channel may not be formed in the first field effect transistor FET1. Therefore, the first field effect transistor FET1 may maintain a turn-off state regardless of whether or not a hydrogen ion exists in the solution 20 to be measured.

When a current flows from the second contact 132 operating as the base terminal of the first and second bipolar junction transistors BJT1 and BJT2 by a current source, the first and second bipolar junction transistors BJT1 and BJT2 are forward-biased. In the BJT mode in which a positive voltage is applied on the reference electrode 161 and a current flows from the second contact 132, the hydrogen ion sensor 100 may show an operation characteristic according a structure itself of the hydrogen ion sensor 100 regardless of whether or not a hydrogen ion exists in the solution 20 to be measured. Therefore, the BJT mode may be used as a pilot mode detecting an operation characteristic of the hydrogen ion sensor 100 itself.

The first and second bipolar junction transistors BJT1 and BJT2 do not operate in the FET mode. For example, when a current is introduced into the second contact 132 operating as the base terminal of the first and second bipolar junction transistors BJT1 and BJT2, the first and second bipolar junction transistors BJT1 and BJT2 are reverse-biased. When a negative voltage is applied on the reference electrode 161, a negative voltage is transferred to the gate terminal of the first field effect transistor FET1 from the reference electrode 161 through the solution 20 to be measured. That is, the first field effect transistor FET1 may change an amount of a channel current according to a hydrogen ion concentration in the solution 20 to be measured.

In the hybrid mode, all of the first and second bipolar junction transistors BJT1 and BJT2, and the first and second field effect transistors FET1 and FET2 operate. For example, when a current flows from the second contact 132 operating as the base terminal of the first and second bipolar junction transistors BJT1 and BJT2, the first and second bipolar junction transistors BJT1 and BJT2 are forward-biased, and when a negative voltage is applied on the reference electrode 161 at the same time, the first field effect transistor FET1 changes an amount of a channel current according to a hydrogen ion concentration in the solution 20 to be measured. In the hybrid mode, a current flowing between the fifth contact 135 and the fourth contact 134 may be represented in a sum of a current flow by the first and second bipolar junction transistors BJT1 and BJT2 and a current flow by the first field effect transistor FET1. Therefore, when the first and second bipolar junction transistors BJT1 and BJT2 are forward-biased by a base current Ib, the hydrogen ion sensor 100 operates like a depletion type field effect transistor.

An operating point of the first and second bipolar junction transistors BJT1 and BJT2 may be adjusted by a bias current applied on the second contact 132. The fifth contact 135 operating as the emitter terminal E may be provided with a voltage source applying an emitter voltage on the fifth contact 135. The first contact 131 operating as the collector terminal S may be connected to a ground node. The fifth contact 135 operating as the emitter terminal E may be used as a sensing node. For example, the hydrogen ion sensor 100 may detect the emitter current Ie flowing into the fifth contact 135 to detect a hydrogen ion concentration in the solution 20 to be measured. Since a current signal has a stronger characteristic with respect to an external noise compared to a voltage signal, when a hydrogen ion concentration in the solution 20 to be measured is detected on the basis of the emitter current, reliability of the hydrogen ion sensor 100 is improved. An operating point (or sensitivity) of the hydrogen ion sensor 100 may be adjusted by changing a reference voltage applied on the reference electrode 161 or changing a base current biased to the second contact 132 operating as the base terminal B.

Figure 5:
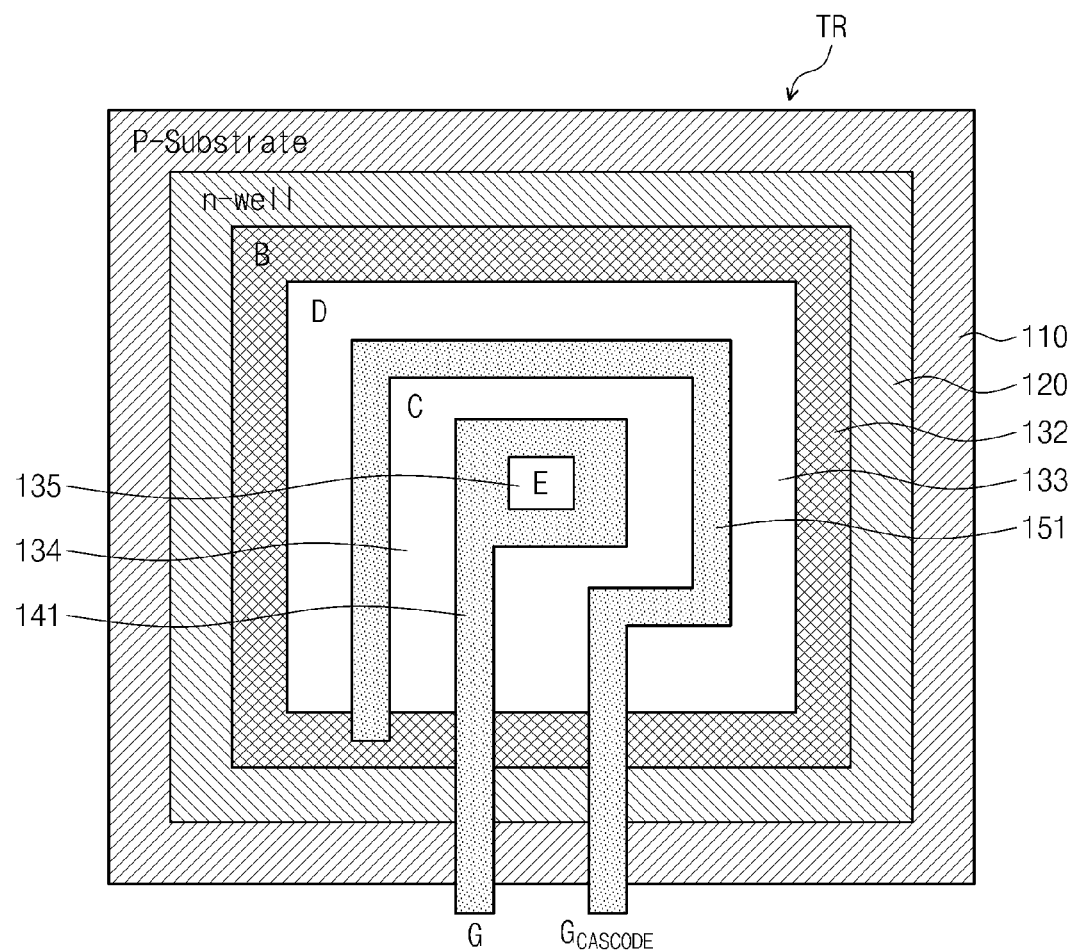
FIG. 5 is a partial plane view illustrating a hydrogen ion sensor according to an embodiment of the present invention.

FIG. 5 is a partial plane view illustrating a hydrogen ion sensor according to an embodiment of the present invention. FIG. 5 illustrates a plane layout of a hydrogen ion sensor 100 except for a hydrogen ion sensing unit 160, that is, a transistor unit TR. The transistor unit TR may be manufactured through a CMOS process. Referring to FIG. 5, the fifth contact 135 operating as the emitter terminal E of the first and second bipolar junction transistors BJT1 and BJT2 and the source terminal of the first field effect transistor FET1 is disposed on a center. The first gate insulation layer 140 operating as the gate insulation layer of the first field effect transistor FET1 and the first conductive layer 141 operating as the gate terminal G of the first field effect transistor FET1 are disposed in a ring shape (for example, a square ring) outside the fifth contact 135. The fourth contact 134 operating as the collector terminal C of the first bipolar junction transistors BJT1 and the drain terminal of the first field effect transistor FET1 and the source terminal of the second field effect transistor FET2 is disposed in a shape ring (for example, a square ring) outside the first conductive layer 141.

The second gate insulation layer 150 operating as the gate insulation layer of the second field effect transistor FET2 and the second conductive layer 151 operating as the gate terminal $G_{CASCODE}$ of the second field effect transistor FET2 are disposed in a ring shape (for example, a square ring) outside the fourth contact 134. The third contact 133 operating as the drain terminal D of the second field effect transistor FET2 is disposed in a ring shape (for example, a square ring) outside the second conductive layer 151. The second contact 132 operating as the base terminal of the first and second bipolar junction transistors BJT1 and BJT2 is disposed in a ring shape (for example, a square ring) outside the third contact 133. The well 120 operating as the base terminal of the first and second bipolar junction transistors BJT1 and BJT2 is disposed outside the second contact 132. The substrate 110 operating as the collector terminal of the second bipolar junction transistor BJT2 is disposed outside the well 120. In addition to, the first contact 131 operating as the collector terminal S of the second bipolar junction transistor BJT2 may be disposed on the substrate 110.

Figure 6:
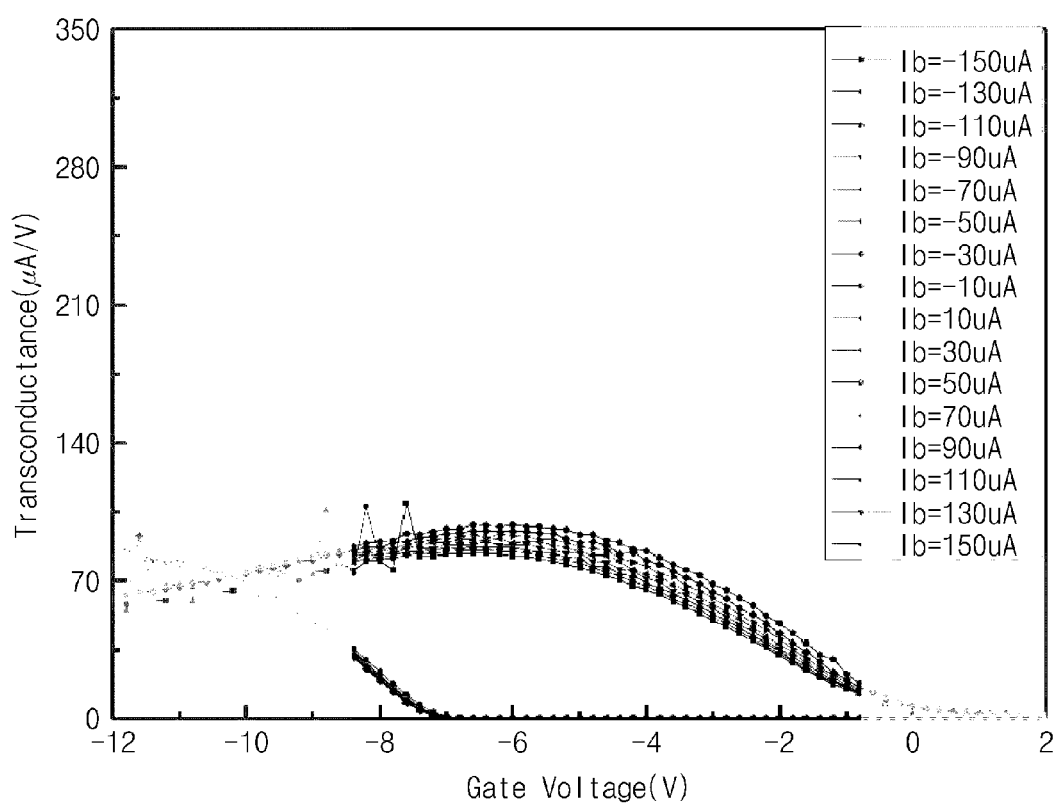
FIG. 6 is a graph showing a change of transconductance of an existing hydrogen ion sensor with respect to each gate voltage.
Figure 7:
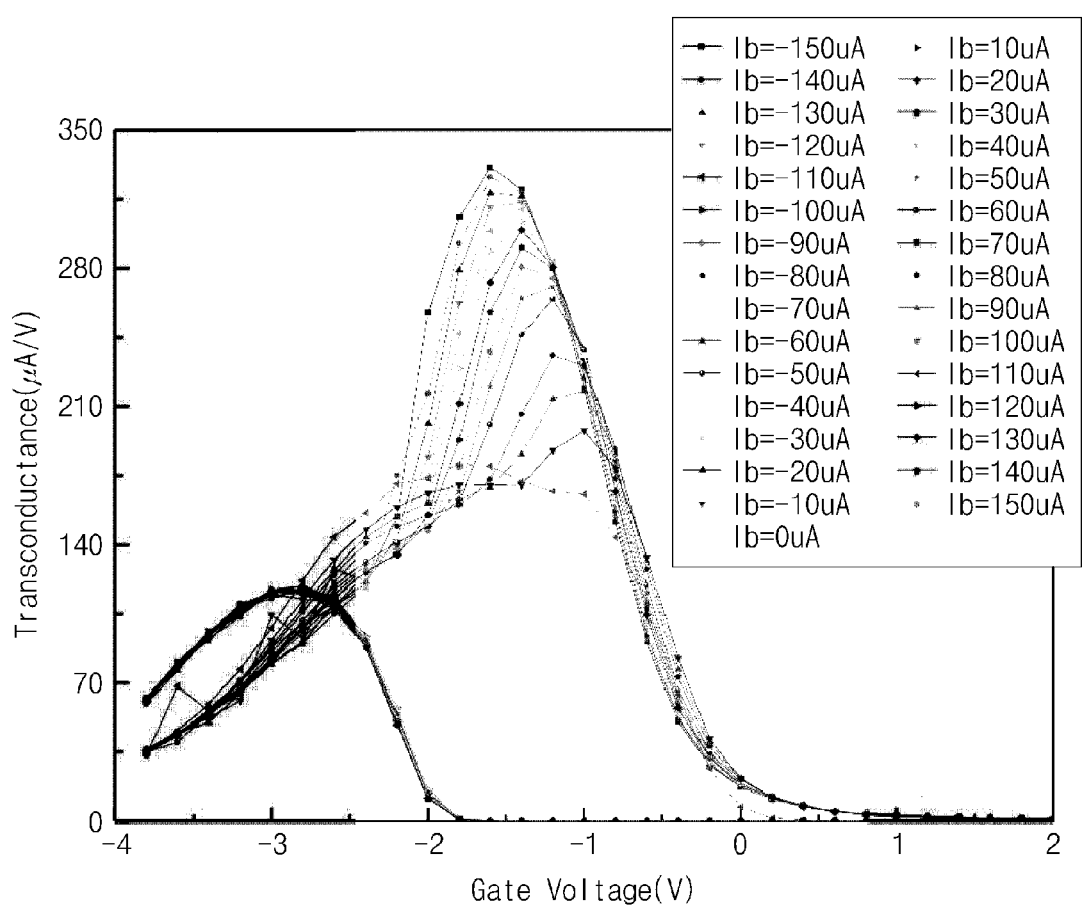
FIG. 7 is a graph showing a change of transconductance of a hydrogen ion sensor according to an embodiment of the present invention with respect to each gate voltage.

FIG. 6 is a graph showing a change of transconductance of an existing hydrogen ion sensor with respect to each gate voltage, and FIG. 7 is a graph showing a change of transconductance of a hydrogen ion sensor according to an embodiment of the present invention with respect to each gate voltage. A gated lateral bipolar junction transistor not including the third contact 133, the second gate insulation layer 150 and the second conductive layer 151 was used as an existing hydrogen ion sensor. That is, the existing hydrogen ion sensor used a structure in which the second field effect transistor FET2 was not connected to the first field effect transistor FET1 and the first bipolar junction transistor BJT1 in a cascode. A base current Ib of the base terminal was changed in a range of about −150 μm to about 150 μm, a voltage $V_G$ of the gate terminal was changed in a range of about −12 to about 2 V in a case of the existing hydrogen ion sensor, and a voltage $V_G$ of the gate terminal was changed in a range of about −4 to about 2 V in a case of the hydrogen ion sensor according to an embodiment of the present invention. As shown in FIGS. 6 and 7, in the case of the hydrogen ion sensor according to an embodiment of the present invention 100, transconductance $g_m$ was improved by about three times greater in average than that of the existing hydrogen ion sensor in which the second field effect transistor was not connected in the cascode. This result means that the hydrogen ion sensor 100 according to an embodiment of the present invention may much more sensitively detect the hydrogen ion.

Figure 8:
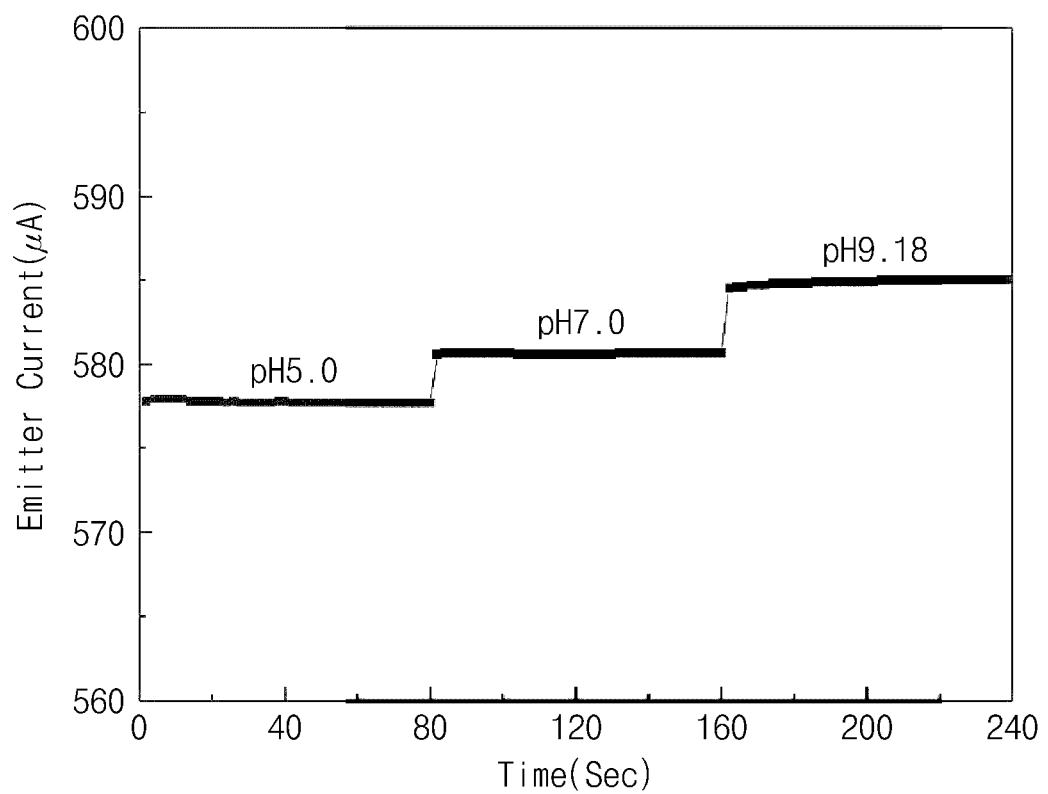
FIG. 8 is a graph showing a change of an emitter current of an existing hydrogen ion sensor with time.
Figure 9:
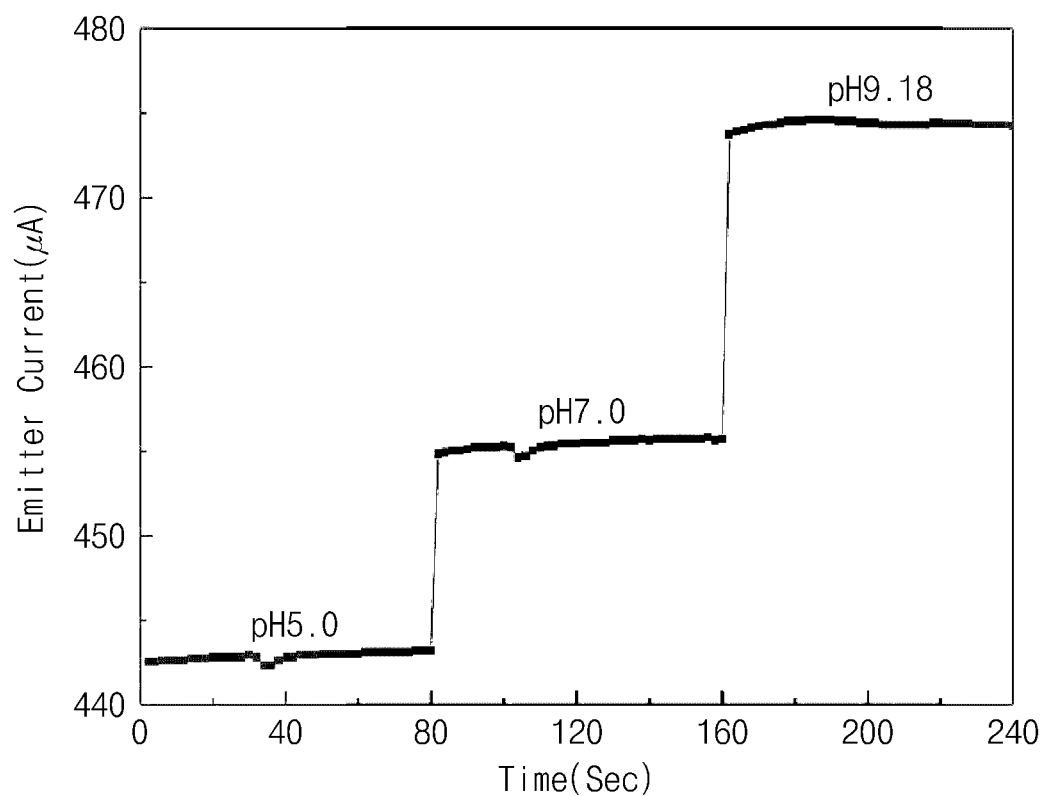
FIG. 9 is a graph showing a change of an emitter current of a hydrogen ion sensor according to an embodiment of the present invention with time.

FIG. 8 is a graph showing a change of an emitter current of an existing hydrogen ion sensor according to a time and FIG. 9 is a graph showing a change of an emitter current of a hydrogen ion sensor according to an embodiment of the present invention with time. A solution to be measured having a pH of about 5.0, a solution to be measured having a pH of about 7.0 and a solution to be measured having a pH of about 9.18 were sequentially supplied, and an emitter current Ie flowing into the emitter terminal E was measured. As shown in FIGS. 8 and 9, the lower the concentration of hydrogen ion is, that is, the higher pH value is, the more an emitter current Ie is increased. As shown in FIGS. 8 and 9, in the hydrogen ion sensor according to an embodiment of the present invention, it may be seen that a change width of the emitter current is much greater than that of the existing hydrogen ion sensor in which the second field effect transistor was not connected in the cascode. This means that the hydrogen ion sensor 100 according to an embodiment of the present invention may more sensitively detect a pH change.

Figure 10:
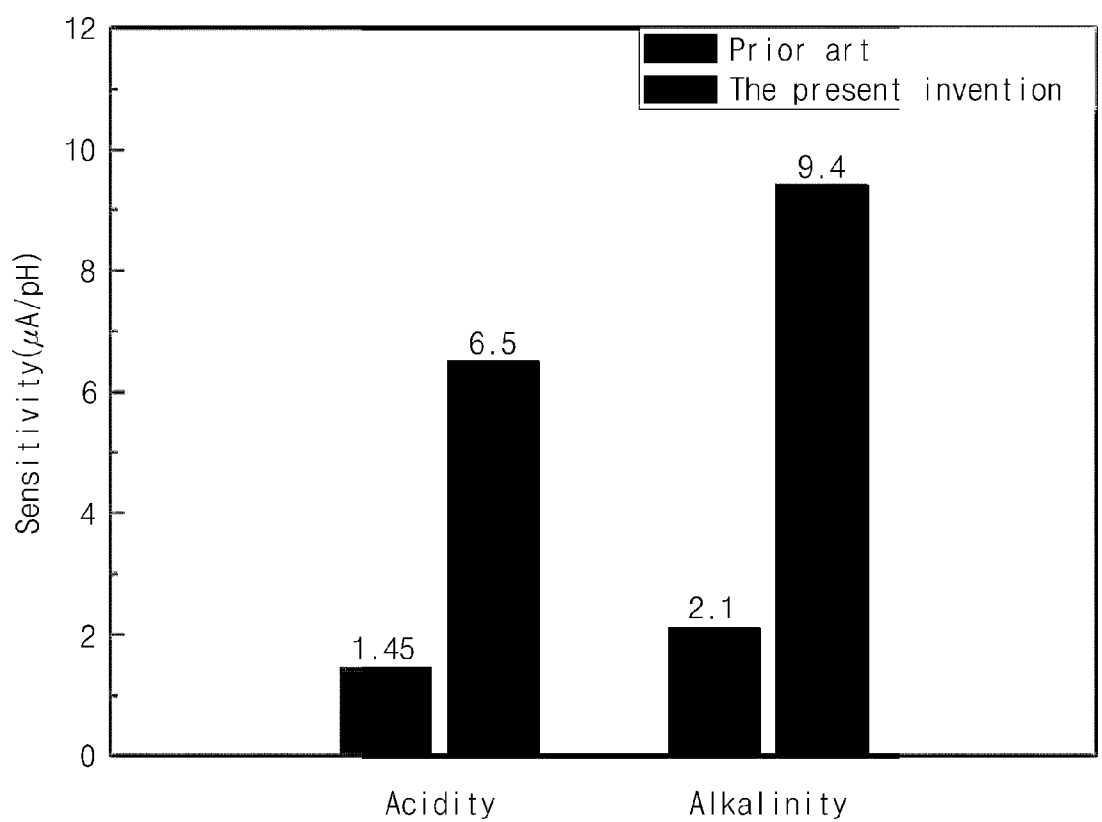
FIG. 10 is a graph showing a comparison between sensitivity of an existing hydrogen ion sensor and sensitivity of a hydrogen ion sensor according to an embodiment of the present invention with time.

FIG. 10 is a graph showing a comparison between sensitivity of an existing hydrogen ion sensor and sensitivity of a hydrogen ion sensor according to an embodiment of the present invention with time. The sensitivity of the hydrogen ion sensor was calculated from a ratio of a change amount of the emitter current Ie with respect to a pH change amount of a solution to be measured. As shown in FIG. 10, in both of a case where a solution to be measured was acidic (pH of about 5.0), and a case where a solution to be measured was alkaline (pH of about 9.18), it may be confirmed that the sensitivity of the hydrogen ion sensor according to an embodiment of the present invention is improved by about 4.5 times greater than the existing hydrogen ion sensor in which the second field effect transistor (the third contact, the second gate insulation layer and the second conductive layer) was not connected in the cascode.

Figure 11:
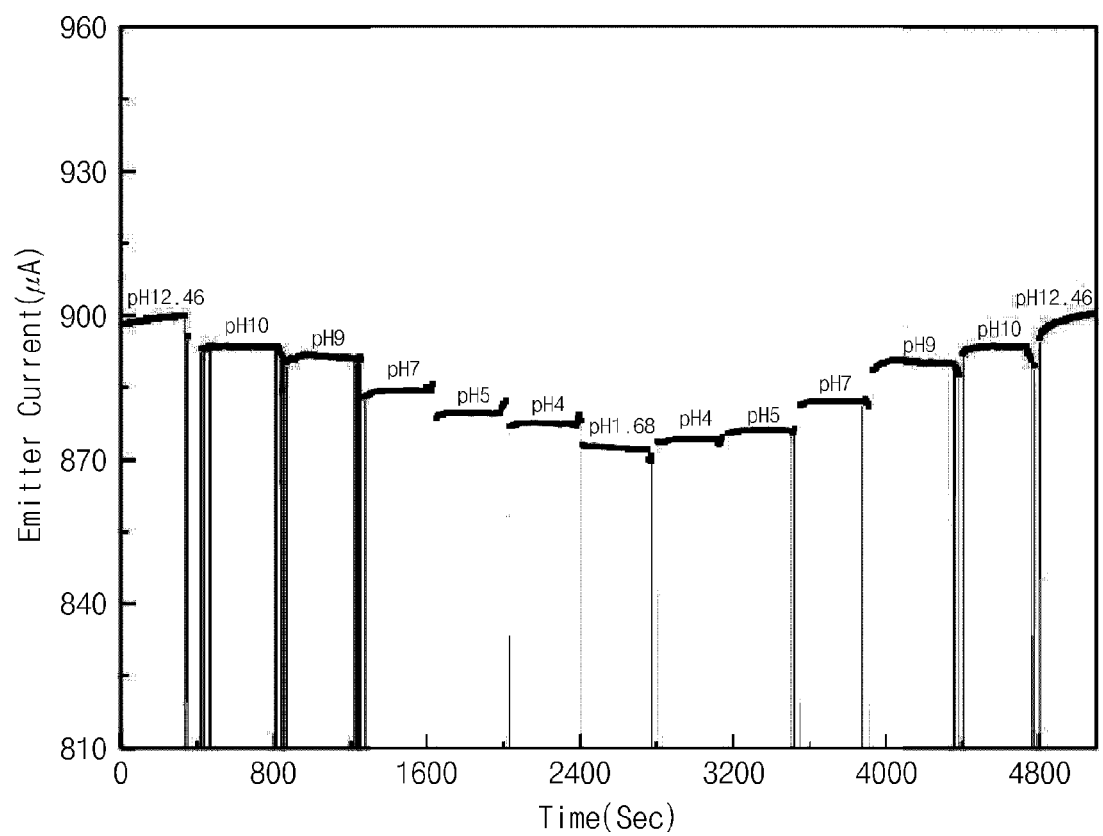
FIG. 11 is a graph showing a change of an emitter current of an existing hydrogen ion sensor with time.
Figure 12:
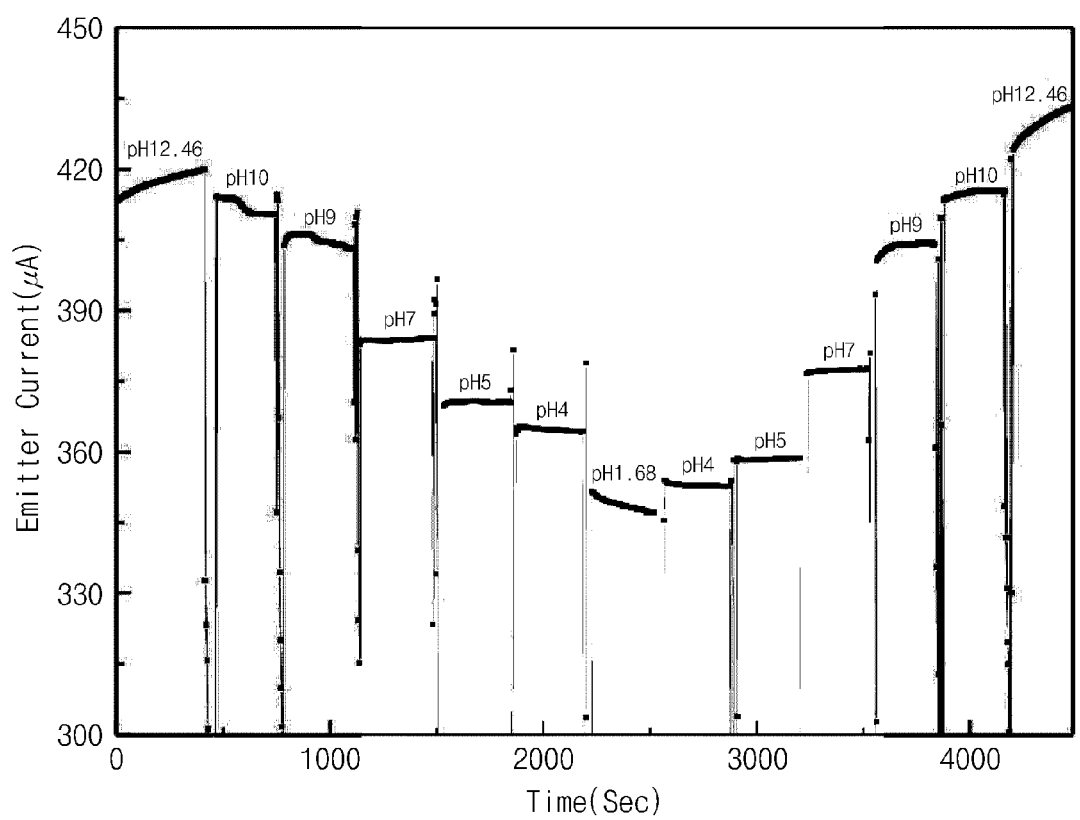
FIG. 12 is a graph showing a change of an emitter current of a hydrogen ion sensor according to an embodiment of the present invention with time.

FIG. 11 is a graph showing a change of an emitter current of an existing hydrogen ion sensor with time, and FIG. 12 is a graph showing a change of an emitter current of a hydrogen ion sensor according to an embodiment of the present invention with time. An emitter current that was measured while pH of a solution to be measured was changed in a range of about 1.68 to about 12.46, and as a result, it may be seen that a change width of an emitter current Ie in the hydrogen ion sensor according to an embodiment of the present invention is improved by about 3 times greater than the existing hydrogen ion sensor in which the second field effect transistor FET2 was not connected in the cascode. As seen from the results of FIGS. 6 to 12, the second field effect transistor FET2 is connected to the first field effect transistor FET1 and the first and second bipolar junction transistors BJT1 and BJT2 in a cascode structure in series, thereby capable of obtaining the hydrogen ion sensor having high sensitivity with respect to a hydrogen ion concentration.

According to an embodiment of the present invention, provided is a high sensitivity hydrogen ion sensor capable of remarkably improving sensitivity with respect to a hydrogen ion concentration.

Also, according to an embodiment of the present invention, provided is a high sensitivity hydrogen ion sensor capable of quantitatively sensing the minimum of a hydrogen ion concentration.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A hydrogen ion sensor comprising:
    a substrate having a well and a first contact, the well having a second, a third, a fourth and a fifth contacts, the second contact having the same conductive type as the well, and the third, the fourth, and the fifth contacts having an opposite conductive type to the well;
    a first gate insulation layer on a region between the fourth contact and the fifth contact;
    a second gate insulation layer on a region between the third contact and the fourth contact; and
    a hydrogen ion sensing unit on the first gate insulation layer,
    wherein the hydrogen ion sensing unit transfers a voltage level adjusted according to a hydrogen ion concentration of a solution to be measured, to the first gate insulation layer,
    wherein the second and the fifth contacts are disposed apart on the well,
    wherein the third contact is disposed between the second contact and the fourth contact,
    wherein the fourth contact is disposed between the third contact and the fifth contact, and
    wherein the fourth contact surrounds the fifth contact in a ring shape.

2. The hydrogen ion sensor of claim 1, further comprising:
    a first conductive layer on the first gate insulation layer; and
    a second conductive layer on the second gate insulation layer.

3. The hydrogen ion sensor of claim 2, wherein the first gate insulation layer and the first conductive layer have a ring shape surrounding the fifth contact, and
    the second gate insulation layer and the second conductive layer have a ring shape surrounding the fourth contact.

4. The hydrogen ion sensor of claim 2, wherein the hydrogen ion sensing unit comprises:
    a reference electrode contacting the solution to be measured, and to which a predetermined reference voltage is applied;
    a measurement electrode measuring the voltage level adjusted according to the hydrogen ion concentration; and
    a floating gate on the first gate insulation layer and transferring the voltage level to the first conductive layer.

5. The hydrogen ion sensor of claim 4, wherein the measurement electrode comprises;
    a first metal layer; and
    a passivation layer on the first metal layer,
    wherein the passivation layer comprises a silicon nitride layer.

6. The hydrogen ion sensor of claim 4, wherein the floating gate comprises a plurality of second metal layers connected to each other through via.

7. The hydrogen ion sensor of claim 1, wherein the well, the fourth contact, the fifth contact and the first gate insulation layer constitute a first field effect transistor, the well, the second contact, the fourth contact and the fifth contact constitute a first bipolar junction transistor, the substrate, the well, the first contact, the second contact and the fifth contact constitute a second bipolar junction transistor, and the well, the third contact, the fourth contact, and the second gate insulation layer constitute a second field effect transistor that is connected in a cascode structure to the first field effect transistor and the first bipolar junction transistor.

8. The hydrogen ion sensor of claim 7, wherein the second filed effect transistor is a field effect transistor of a N-channel type or a P-channel type.

9. The hydrogen ion sensor of claim 7, wherein the first contact operates as a collector terminal of the second bipolar junction transistor, the second contact operates as a base terminal of the first bipolar junction transistor and the second bipolar junction transistor, the third contact operates as a drain terminal of the second field effect transistor, the fourth contact operates as a drain terminal of the first field effect transistor, a source terminal of the second field effect transistor and a collector terminal of the first bipolar junction transistor, and the fifth contact operates as a source terminal of the first field effect transistor and an emitter terminal of the first bipolar junction transistor and the second bipolar junction transistor.

10. The hydrogen ion sensor of claim 9, wherein an operating point of the first bipolar junction transistor and the second bipolar junction transistor is adjusted by a bias current applied on the second contact.

11. The hydrogen ion sensor of claim 9, wherein the hydrogen ion concentration is detected by detecting an amount of a current flowing through the fifth contact.

* * * * *